(12) United States Patent
Arnold et al.

(10) Patent No.: US 6,881,702 B2
(45) Date of Patent: Apr. 19, 2005

(54) METHOD FOR PRODUCING A MULTI METAL OXIDE CATALYST, METHOD FOR PRODUCING UNSATURATED ALDEHYDES AND/OR CARBOXYLIC ACIDS AND BAND CALCINATION DEVICE

(75) Inventors: Heiko Arnold, Mannheim (DE); Signe Unverricht, Mannheim (DE); Raimund Felder, Neustadt (DE); Klaus Harth, Altleiningen (DE); Klaus Joachim Müller-Engel, Stutensee (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/363,856

(22) PCT Filed: Sep. 20, 2001

(86) PCT No.: PCT/EP01/10911

§ 371 (c)(1),
(2), (4) Date: Mar. 14, 2003

(87) PCT Pub. No.: WO02/24620

PCT Pub. Date: Mar. 28, 2002

(65) Prior Publication Data

US 2004/0034249 A1 Feb. 19, 2004

(30) Foreign Application Priority Data

Sep. 21, 2000 (DE) .......................... 100 46 957

(51) Int. Cl.⁷ ................... B01J 23/00; B01J 27/192; B01J 21/08; B01J 21/12; B01J 21/14
(52) U.S. Cl. ................. 502/311; 502/212; 502/240; 502/248; 502/255; 502/321
(58) Field of Search ................. 502/212, 240–261, 502/305–322

(56) References Cited

U.S. PATENT DOCUMENTS

| | | | |
|---|---|---|---|
| 4,330,429 A | 5/1982 | Sasaki et al. | |
| 4,438,217 A | 3/1984 | Takata et al. | |
| 4,534,780 A | 8/1985 | Cemin | |
| 4,719,332 A | 1/1988 | Markuson, Jr. | |
| 4,837,191 A * | 6/1989 | Glaeser et al. | 502/202 |
| 4,837,360 A | 6/1989 | Kadowaki et al. | |
| 5,198,581 A | 3/1993 | Kawajiri et al. | |
| 5,276,178 A | 1/1994 | Onodera et al. | |
| 5,364,825 A | 11/1994 | Neumann et al. | |
| 5,637,546 A | 6/1997 | Tenten et al. | |
| 6,383,976 B1 * | 5/2002 | Arnold et al. | 502/311 |
| 6,395,936 B1 * | 5/2002 | Arnold et al. | 568/476 |
| 6,403,829 B1 * | 6/2002 | Unverricht et al. | 562/532 |
| 6,428,765 B1 * | 8/2002 | Bedard et al. | 423/594.8 |
| 6,444,845 B1 * | 9/2002 | Karim et al. | 562/535 |
| 6,737,545 B1 * | 5/2004 | Hibst et al. | 562/535 |

FOREIGN PATENT DOCUMENTS

| | | |
|---|---|---|
| EP | 0 000 835 | 9/1981 |
| EP | 0 275 671 | 7/1988 |
| EP | 0 750 942 | 1/1997 |
| EP | 0 807 465 | 11/1997 |
| EP | 0 900 774 | 3/1999 |
| JP | 08 086571 | 4/1996 |
| WO | 01 36364 | 5/2001 |

* cited by examiner

Primary Examiner—Cam N. Nguyen
(74) Attorney, Agent, or Firm—Oblon, Spivak, McClelland, Maier & Neustadt, P.C.

(57) ABSTRACT

A catalyst suitable for the gas-phase oxidation of organic compounds to $\alpha,\beta$-unsaturated aldehydes and/or carboxylic acids and having an active phase comprising a multimetal oxide material is prepared by a process in which a particulate catalyst precursor which contains oxides and/or compounds of the elements other than oxygen which constitute the multimetal oxide material, which compounds can be converted into oxides, is prepared and said catalyst precursor is converted by calcination into a catalytically active form, wherein a stream of the particulate catalyst precursor is passed at substantially constant speed through at least one calcination zone at constant temperature for calcination.

11 Claims, 2 Drawing Sheets

METHOD FOR PRODUCING A MULTI METAL OXIDE CATALYST, METHOD FOR PRODUCING UNSATURATED ALDEHYDES AND/OR CARBOXYLIC ACIDS AND BAND CALCINATION DEVICE

Preparation of a multimetal oxide catalyst, preparation of unsaturated aldehydes and/or carboxylic acids and belt calcination apparatus The present invention relates to a process for the preparation of a catalyst comprising an active phase of a multimetal oxide material, a process for the preparation of $\alpha,\beta$-monoethylenically unsaturated aldehydes and/or carboxylic acids using the catalyst and a belt calcination apparatus which is designed especially for the preparation of the catalyst.

While acrylic acid and acrylates were prepared predominantly by the Reppe process even toward the end of the 60s, the preparation by gas-phase oxidation of propene predominates today. The oxidation of propene to acrylic acid can be carried out in one stage or two stages. Catalysts used for the heterogeneously catalyzed reaction are as a rule multimetal oxide materials which generally contain heavy metal molybdates as main component and compounds of various elements as promoters. The oxidation of propene takes place in a first step to give acrolein and in a second step to give acrylic acid. Since the two oxidation steps may differ in their kinetics, uniform process conditions and a single catalyst do not as a rule lead to optimum selectivity. Recently, two-stage processes with optimum adaptation of catalyst and process variables have therefore preferably been developed. In general, propene is oxidized to acrolein in the presence of molecular oxygen in the first stage in an exothermic reaction in a fixed-bed tubular reactor. The reaction products are passed directly into the second reactor and are further oxidized to acrylic acid. The reaction gases obtained in the second stage can be condensed and the acrylic acid can be isolated therefrom by extraction and/or distillation.

The oxidation of propene to acrolein and/or acrylic acid is highly exothermic. The tubes of the fixed-bed tubular reactor which are filled with the heterogeneous catalyst are therefore surrounded by a cooling medium, as a rule a salt melt, such as a eutectic mixture of $KNO_3$ and $NaNO_2$. The heat of reaction is released through the wall of the catalyst-filled tubes to the salt bath. In spite of the cooling by the cooling medium, a uniform temperature is not established over the length and/or the cross section of the catalyst-filled tubes. Overheated regions, i.e. hot spots, form. Thus, the propene concentration of the reaction mixture in the vicinity of the entrance of the catalyst-filled tubes is high while the reaction mixture in the vicinity of the exit has a lower propene concentration, promoting the formation of overheated regions in the vicinity of the entrance. Since the reaction rate generally increases with increasing temperature, an inhomogeneous temperature distribution leads to additional conversion in the warmer regions, the exothermic heat evolution associated therewith leading to greater disequilibrium of the temperature.

The formation of overheated regions in the catalyst-filled tubes is disadvantageous for various reasons. Excessive oxidation beyond the desired oxidation state occurs in the overheated regions. Furthermore, the excessive thermal stress influences the catalyst performance and catalyst life. The formation of overheated region can finally lead to an uncontrolled course of the reaction, which can result in an explosive runaway reaction. The excessive formation of overheated regions is disadvantageous in particular in the case of molybdenum-based catalysts, since molybdenum compounds tend to sublime.

For standardizing the temperature profile in the catalyst-filled tubes, it has been proposed to use catalysts of different activities in the tubes, the catalyst activities increasing axially in the direction of flow of the reaction mixture. Catalysts of different activity can be obtained, for example, by varying the chemical composition, cf. U.S. Pat. No. 5,276,178 and DE 30 06 894. On the other hand, the catalyst activity can also be varied by varying the calcination temperature during the catalyst preparation, cf. WO 98/24746. U.S. Pat. No. 5,198,581 recommends using catalysts of different volume ratios, the volume ratio decreasing axially in the direction of flow of the reaction mixture. These proposals are disadvantageous in that the preparation of a plurality of catalysts of different activity and the structured filling of the catalyst into the reaction tubes is complicated and time-consuming.

U.S. Pat. No. 4,438,217 recommends the use of specific catalyst geometries before reducing the problems of the formation of overheated regions. EP 0 807 465 describes a catalyst having a defined proportion of active phase, particle size of the catalyst and calcination temperature.

JP 08086571-A describes a treatment apparatus which comprises a belt conveyor having a gas-permeable belt, which revolves within a hollow cylindrical housing, and an apparatus by means of which a gas can be passed to the conveying part of the belt inside the path of the revolving belt.

It is an object of the present invention to provide a catalyst having an active phase of a multimetal oxide material and a process for its preparation which, when used for the preparation of $\alpha,\beta$-monoethylenically unsaturated aldehydes and/or carboxylic acids, permits substantial optimization of the equilibrium of activity, selectivity and catalyst life.

It was found that the problems described above in connection with the formation of the hot spots in the case of catalysts prepared by known processes are superimposed and exacerbated by fluctuations in the activity of the individual catalyst particles over a given population of catalyst particles which are contained in an industrial fixed-bed tubular reactor. The heterogeneous catalysts used and comprising an active phase of a multimetal oxide material have, depending on their chemical composition and preparation conditions, a temperature range in which activity, selectivity and catalyst life are optimally balanced. If particles having greatly differing activities are present in a population of the catalyst particles in a reactor, part of the catalyst is inevitably operated at a temperature which is more or less far away from the optimum temperature range of the respective catalyst particles. This is associated with declines in the yield, selectivity and catalyst life.

With the present invention, it was found that the use of a population of catalyst particles having a substantially homogeneous activity, i.e., having a very narrow activity distribution, permits optimization of the preparation of $\alpha,\beta$-monoethylenically unsaturated aldehydes and/or carboxylic acids with regard to yield, selectivity and catalyst life. Usually, an industrial reactor for the preparation of $\alpha,\beta$-monoethylenically unsaturated aldehydes and/or carboxylic acids contains several tons of catalyst. The prior art provides no indication as to how a very narrow activity distribution can be achieved over such a large amount of catalyst. The apparatuses usually used for the calcination, such as muffle furnaces or tray furnaces, either permit only the preparation of small amounts of catalyst or, if they have a sufficiently large capacity, have an insufficient temperature constancy. Since, as shown in the examples and comparative examples below, even small differences in the calcination temperature can lead to greatly varying activity, insufficient temperature constancy during the calcination leads to catalyst batches having greatly fluctuating activity. The mixing of a large amount with catalyst of fluctuating activity to standardize the activity has substantial disadvantages. On the one hand, the catalyst is exposed, during the mixing process, to mechanical stress which leads to abrasion in the case of coated catalysts and to breakages in the case of extrudates and catalyst pellets. On the other hand, only standardization at a low level is achieved by mixing since activity differences between the individual catalyst particles also remain on mixing.

We have found that this object is achieved by a process for the simple and economical preparation of large amounts of a catalyst comprising an active phase of a multimetal oxide material having a narrow activity distribution.

The present invention relates to a process for the preparation of a catalyst suitable for the gas phase oxidation of organic compounds to α,β-unsaturated aldehydes and/or carboxylic acids and having an active phase of a multimetal oxide material, in which a particulate catalyst precursor which contains oxides and/or compounds of the elements other than oxygen which constitute the multimetal oxide material, which compounds can be converted into oxides, is prepared and said catalyst precursor is converted by calcination into a catalytically active form, wherein a stream of the particulate catalyst precursor is passed at substantially constant speed through at least one calcination zone for calcination, the maximum variation of the temperature as a function of time and the maximum local temperature difference in the calcination zone each being ≦5° C.

Catalysts prepared according to the invention may be present both as unsupported catalysts and as supported catalysts. In the case of the unsupported catalysts, the catalyst substantially comprises the multimetal oxide material. The corresponding catalyst precursor substantially comprises a thorough mixture of oxides and/or compounds of the elements other than oxygen which constitute the multimetal oxide material, which compounds can be converted into oxides. The mixture is compacted to the desired catalyst geometry, for example by pelleting or extrusion, if required with the use of conventional assistants, such as lubricants and/or molding assistants, such as graphite or stearic acid, or reinforcing materials, such as microfibers of glass, asbestos, silicon carbide or calcium titanate. The unsupported catalysts may have any desired geometry, such as cylindrical, spherical, etc.; preferred catalyst geometries are hollow cylinders, for example having an external diameter and a length of from 2 to 10 mm and a wall thickness of from 1 to 3 mm.

In order to obtain catalyst precursors for supported catalysts prepared according to the invention, supports are expediently coated with a generally thorough powder mixture of oxides and/or compounds of the elements other than oxygen which constitute multimetal oxide material, which compounds can be converted into oxides. Expediently, the powder material to be applied can be moistened for coating the supports and, after application, can be dried, for example by means of hot air. The coat thickness of the powder material applied to the support is expediently chosen to be in the range from 50 to 500 µm, preferably from 100 to 350 µm. The support materials used may be conventional porous or nonporous aluminas, silica, thorium dioxide, zirconium dioxide, silicon carbide or silicates, such as magnesium silicate or aluminum silicate. The supports may have a regular or irregular shape, regularly shaped supports having preferably substantial surface roughness, e.g. spheres or hollow cylinders, being preferred.

The multimetal oxide material may be present in amorphous and/or crystalline form. It may contain crystallites of a defined crystal structure type or mixtures of such crystallites. The multimetal oxide material may have a substantially uniform composition of the mixture or may contain regions of a dispersed phase whose chemical composition differs from that of its local environment. This is the case, for example, with key phases or promoter phases which are dispersed in a host phase. The regions of differing chemical composition preferably have a maximum diameter of from 1 to 25 µm, in particular from 1 to 20 µm, and particularly preferably from 5 to 15 µm, the maximum diameter being regarded as the longest connecting line between two points present on the surface of the particle which passes through the center of gravity of a particle. As a rule, the dispersed phase is prepared separately beforehand in finely divided form and mixed with oxides and/or compounds of the elements other than oxygen which constitute the host phase of the multimetal oxide material, which compounds can be decomposed into oxides.

Particularly suitable compounds, which as a rule can be converted into oxides by heating in the presence or absence of oxygen, are halides, nitrates, formates, oxalates, citrates, acetates, carbonates, amine complex salts, ammonium salts and/or hydroxides. Compounds such as ammonium hydroxide, ammonium carbonate, ammonium nitrate, ammonium formate, ammonium acetate, ammonium oxalate or acetic acid, which decompose and/or can be decomposed on calcination substantially completely to give compounds escaping in gaseous form, can be additionally incorporated as pore formers. The oxides and/or compounds of the elements other than oxygen which constitute the multimetal oxide material, which compounds can be converted into oxides, are preferably thoroughly mixed. The thorough mixing can be effected in dry or in wet form. If it is effected in dry form, the starting compounds are expediently used in the form of finely divided powders. Preferably, however, the thorough mixing is effected in wet form. Usually, the starting compounds are mixed with one another in the form of an aqueous solution and/or suspension. The aqueous material obtained is then dried, the drying process preferably being carried out by spray-drying of the aqueous mixture.

Catalysts comprising an active phase of a multimetal oxide material for the preparation of α,β-monoethylenically unsaturated aldehydes and/or carboxylic acids by gas-phase oxidation of an alkane, alkanol, alkene and/or alkenal of 3 to 6 carbon atoms are known per se and are described, for example, in EP 0 000 835, EP 0 575 897, DE 198 55 913, U.S. Pat. No. 5,276,178, DE 30 06 894, U.S. Pat. No. 5,198,581, WO 98/24746, U.S. Pat. No. 4,438,217 and EP 0 807 465.

These catalysts are suitable in particular for the preparation of α,β-monoethylenically unsaturated aldehydes and/or carboxylic acids in a high-load procedure.

The multimetal oxide materials preferably contain at least one first metal selected from molybdenum and tungsten and at least one second metal selected from bismuth, tellurium, antimony, tin, copper, iron, cobalt and/or nickel.

Particularly preferred multimetal oxide materials have the formula I or II $$[X^1_a X^2_b O_x]_p [X^3_c X^4_d X^5_e X^6_f X^7_g X^2_h O_y]_q \qquad (I)$$

$$Mo_{12} Bi_i X^8_k Fe_l X^9_m X^{10}_n O_z \qquad (II)$$

where $X^1$ is bismuth, tellurium, antimony, tin and/or copper, preferably bismuth, $X^2$ is molybdenum and/or tungsten, $X^3$ is an alkali metal, thallium and/or samarium, preferably potassium, $X^4$ is an alkaline earth metal, nickel, cobalt, copper, manganese, zinc, tin, cadmium and/or mercury, preferably nickel and/or cobalt, $X^5$ is iron, chromium, cerium and/or vanadium, preferably iron, $X^6$ is phosphorus, arsenic, boron and/or antimony, $X^7$ is a rare earth metal, titanium, zirconium, niobium, tantalum, rhenium, ruthenium, rhodium, silver, gold, aluminum, gallium, indium, silicon, germanium, lead, thorium and/or uranium, preferably silicon, aluminum, titanium and/or zirconium, a is from 0.01 to 8, b is from 0.1 to 30, c is from 0 to 4, d is from 0 to 20, e is from 0 to 20, f is from 0 to 6, g is from 0 to 15, h is from 8 to 16, x and y are numbers which are determined by the valency and frequency of the elements other than oxygen in I, p and q are numbers whose ratio p/q is from 0.1 to 10, $X^8$ is cobalt and/or nickel, preferably cobalt, $X^9$ is silicon and/or aluminum, preferably silicon, $X^{10}$ is an alkali metal, preferably potassium, sodium, cesium and/or rubidium, in particular potassium, i is from 0.1 to 2, k is from 2 to 10, l is from 0.5 to 10, m is from 0 to 10, n is from 0 to 0.5, z is a number which is determined by the valency and frequency of the elements other than oxygen in II.

The novel process is particularly suitable for the preparation of catalysts comprising an active phase of a multimetal oxide material of the formula II, since these materials have a particularly pronounced dependence of the activity on the calcination temperature.

Multimetal oxide materials of the formula I are known per se from EP 0 000 835 and EP 0 575 897 and multimetal oxide materials of the formula II are known per se from DE 198 55 913; these publications are hereby incorporated by reference in their entirety.

Multimetal oxide materials of the formula I contain three-dimensional, delimited regions of the chemical composition $X^1_a X^2_b O_x$, whose chemical composition differs from that of their local environment. The maximum diameter of the delimited regions is preferably from 1 to 25 µm, in particular from 1 to 20 µm, and particularly preferably from 5 to 15 µm. Catalyst precursors for catalysts comprising an active phase of a multimetal oxide material of the formula I are obtained in a suitable manner by first preforming a calcined oxide $X^1_a X^2_b O_x$ by mixing, for example, water-soluble salts of $X^1$ with oxo acids or their ammonium salts of $X^2$ in aqueous solution, drying the solution and calcining the dried material, if necessary comminuting the oxide obtained and separating off particles of a desired particle class. The separately preformed oxide is then mixed with oxides and/or compounds of $X^3$, $X^4$, $X^5$, $X^6$, $X^7$ and $X^2$ which can be converted into oxides, in desired stoichiometric ratios, and, if the mixing is effected in the wet state, the mixture is dried.

Catalyst precursors for catalysts comprising an active phase of a multimetal oxide material of the formula II are obtained in a suitable manner by preparing a first aqueous solution of compounds of the elements bismuth, iron and $X^8$, preparing a second aqueous solution of compounds of the elements molybdenum and $X^{10}$, mixing the first and second aqueous solutions, the first or the second aqueous solution or a mixture thereof being mixed with a solution or suspension of a compound of the element $X^9$, and drying the resulting mixture or precipitated product, preferably by spray-drying.

For the final calcination, a stream of th particulate catalyst precursor, preferably a mass flow which is substantially constant as a function of time, is passed through at least one calcination zone at substantially constant speed. The term calcination is intended here also to include thermal treatment steps, such as final drying and/or decomposition, which are upstream of the actual calcination. Expediently, the stream of the particulate catalyst precursor is passed in succession through at least two, for example from two to ten, calcination zones, which as a rule are thermostated at different temperatures. In this way, it is possible to realize different temperature profiles through which the stream of the particulate catalyst precursor passes. For example, the successive calcination zones can be thermostated, for example, at temperatures increasing stepwise. The individual calcination zones may have different spatial dimensions, so that different residence times in the individual calcination zones result at constant speed of the stream of the particulate catalyst precursor.

In at least one calcination zone, the catalyst precursor is heated to a temperature of in general from 400 to 600° C., preferably from 450 to 530° C. When the novel process is carried out using eight calcination zones, for example, the following temperature profile is suitable:

1: 100–200° C.; 2: 150–250° C.; 3: 200–300° C.; 4: 250–350° C.;

5: 350–400° C.; 6: 400–550° C.; 7: 400–550° C.; 8: 400–550° C.

With the use of three zones, the following temperature profile is suitable:

1: 100–400° C.; 2: 250–550° C.; 3: 400–550° C.

With the use of four zones, the following temperature profile is suitable:

1: 100–250° C.; 2: 200–350° C.;

3: 350–550° C.; 4: 400–550° C.

With the use of six zones, the following temperature profile is suitable:

1: 100–200° C.; 2: 150–300° C.; 3: 200–350° C.;

4: 300–400° C.; 5: 400–500° C.; 6: 400–600° C.

With the use of 12 zones, the following temperature profile is suitable:

1: 100–200° C.; 2: 150–250° C.; 3: 200–300° C.; 4: 250–350° C.;

5: 350–400° C.; 6: 400–500° C.; 7: 400–550° C.; 8: 400–550° C.;

9: 400–600° C.; 10: 400–600° C.; 11: 400–700° C.; 12: 400–700° C.

In order to carry out the novel process successfully, it is essential for the temperature in the calcination zone (in the calcination zones) to be substantially constant locally and as a function of time. The temperature constancy can be checked by means of temperature measuring apparatuses, for example thermocouples. Preferably at least 4, in particular at least 6, particularly preferably at least 10, thermocouples are provided per calcination zone and are arranged as far as possible equidistant over the calcination zone. Preferably, the mean value of the hourly mean values of the temperature measured at the individual thermocouples of a calcination zone differs by not more than 5° C., in particular not more than 3° C., particularly preferably not more than 2° C., from the respective setpoint value. The record of the temperatures measured at the individual thermocouples and the calculation of the mean values are expediently carried out automatically by an appropriately programmed computer. This advantageously also regulates or controls the heating of the calcination zones. The thermocouples are advantageously regularly calibrated in order to ensure that the maximum deviation of the measured temperature from the actual temperature is preferably less than 0.5° C.

The maximum variation of the temperature in the calcination zone (in the calcination zones) as a function of time is ≦5° C., in particular ≦3° C., particularly preferably ≦2° C. The variation of the temperature as a function of time is regarded as the standard deviation of the temperature measured at an individual thermocouple of a calcination zone over one hour. The maximum local temperature difference, i.e. the maximum temperature difference within the calcination zone (in the calcination zones) is ≦5° C., in particular ≦3° C., particularly preferably ≦2° C. The local temperature difference is regarded as the standard deviation of the hourly mean values of the temperatures measured at the thermocouples of a calcination zone.

The atmosphere in the calcination zone may consist of inert gas, e.g. nitrogen or argon, a mixture of inert gas and oxygen, e.g. air, reducing gases, such as hydrocarbons, e.g. methane, aldehydes, e.g. acrolein or ammonia, or of a mixture of oxygen and reducing gases. In the calcination under reducing conditions, however, it should be ensured that the metallic constituents are not reduced to the element. Expediently, an oxygen-containing gas, in particular air, is therefore present in the calcination zone. In order to achieve the uniform temperature in the calcination zone and/or to transport away any decomposition gases formed, it is preferable to pass a stream of a gas over the catalyst precursor, perpendicularly to the direction of advance of the catalyst precursor in the calcination zone. Suitable gases are the abovementioned ones, in particular air. Particularly for the preparation of catalysts comprising a molybdenum- and bismuth-containing multimetal oxide material, it may be advantageous to carry out the calcination in an atmosphere which contains 1% by volume or more of nitric oxide and 0.5% by volume or more of oxygen, as described in EP-A-558 028.

For carrying out the novel process, it is expedient to use a belt calcination apparatus comprising at least one heatable chamber and a conveyor belt passing through the chamber and intended for holding the particulate catalyst precursor. The conveyor belt is as a rule a continuous belt which can be advanced horizontally through the heatable chamber and forms at its one end an ascending reverse path and at its other end a descending reverse path. It is often advantageous to provide a housing within which the conveyor belt revolves, i.e. which surrounds the chamber(s) and the ascending and descending reverse paths. Means for feeding the particulate catalyst precursor onto the conveyor belt are expediently provided in the vicinity of the ascending reverse path and means for removing the calcined catalyst from the conveyor belt are expediently provided at the descending reverse path. The means for feeding consists, for example, of a shaft filled with the particulate catalyst precursor, a bed of the catalyst precursor having a substantially constant layer thickness being withdrawn under the shaft by the movement of the conveyor belt. The shaft expediently has a scraping apparatus, for example an adjustable weir. At the descending reverse path, the calcined catalyst is ejected from the conveyor belt and expediently collected by suitable means. If, as in a preferred embodiment, the gas is passed over the catalyst precursor in the calcination zone, the conveyor belt is gas-permeable and consists, for example, of a perforated belt or woven fabric or knitted fabric of metal wire or another heat-resistant material. The speed of the conveyor belt is as a rule from about 0.1 to cm/min. In order to pass the particulate catalyst precursor in succession through a plurality of calcination zones of different temperatures, a belt calcination apparatus which comprises at least two, for example from two to ten, heatable chambers which can be regulated to different temperatures is expediently used.

The heating of the chamber(s) can be effected in various ways, for example by electrical heating by means of resistance elements, for example installed in the chamber wall. However, the heating is preferably effected indirectly, i.e. by means of heat sources, such as burners, which are arranged outside the chamber(s), suitably below the chamber(s). The burners are operated with a combustible gas, such as natural gas.

In the chamber (the chambers) of the belt calcination apparatus, the calcination zone is defined by the width of the support area of the conveyor belt and the maximum bed height of the particulate catalyst precursor on the conveyor belt. The thermocouples provided for monitoring the temperature constancy in the calcination zone are preferably distributed uniformly over the support area of the conveyor belt and the bed height. In order to achieve very high local temperature constancy in the calcination zone, the atmosphere in the heatable chambers is preferably circulated. A belt calcination apparatus specially designed for carrying out the novel process therefore has, in the chamber, means for producing a gas circulation on the basis of forced convection. Such a belt calcination apparatus as such is novel and is a further subject of the present invention.

The present invention therefore relates, in a further aspect, to a belt calcination apparatus comprising at least one heatable chamber and a gas-permeable conveyor belt passing through the chamber and intended for holding a particulate material, wherein means for producing a gas circulation on the basis of forced convection are provided in the chamber.

In a preferred embodiment, the means for producing the gas circulation comprise a fan, which is suitably arranged above the conveyor belt in the chamber (the chambers). In suitable embodiments, the means for producing the gas circulation also comprise gas-guiding apparatuses for guiding the gas circulation inside the chamber, the gas-guiding apparatuses inside the chamber extending in each case along the edge of the conveyor belt, substantially in a plane perpendicular to the support area of the conveyor belt. The means for producing the gas circulation and/or the gas-guiding apparatuses are expediently formed in such a way that the gas ascends through the gas-permeable conveyor belt and the bed of particulate catalyst precursor present thereon and descends again along the walls of the chamber. However, a gas circulation in the opposite direction is also possible. If the belt calcination apparatus has at least two heatable chambers, these are preferably delimited relative to one another in such a way that substantially no gas exchange takes place between the chambers. For removal of decomposition gases and the like, some of the gas circulating in the chamber is preferably removed continuously or periodically and replaced by fresh gas. The supply of fresh gas is controlled in such a way that the temperature constancy in the chamber is not adversely affected. The volume of the gas circulated by unit time in the chamber is as a rule greater than the volume of the gas fed into or removed from the chamber per unit time and is preferably at least five times the amount.

If desired, it is also possible to pass in succession through a plurality of the belt calcination apparatuses described above, for example two or three thereof, in order to optimize the different heats of reaction in individual steps, for example by varying the bed height and/or residence time. After passing through one apparatus and before passing through a further apparatus, the catalyst precursor can, if required, be collected and temporarily stored.

By means of the novel process, large amounts of a catalyst which is suitable for the preparation of α,β-monoethylenically unsaturated aldehydes and/or carboxylic acids by gas-phase oxidation of organic compounds, e.g. alkanes, alkanols, alkenes and/or alkenals of 3 to 6 carbon atoms and has an active phase of a multimetal oxide material can be obtained with a narrow activity distribution within the batch prepared. For the purposes of the present invention, the activity of the catalyst is defined as the temperature at which a propene conversion of 95% is obtained if a mixture of 5% by volume of propene, 9.5% by volume of oxygen and 85.5% by volume of nitrogen is passed over 100 g of catalyst at 100 l (S.T.P.)/h (volume at standard temperature (0° C.) and pressure (1013 mbar)). An experimental setup as described further below is suitable for the determination.

In a further aspect, the present invention relates to a batch of at least 100 kg, in particular at least 300 kg, particularly preferably at least 1 t (metric ton) of a catalyst which has a multimetal oxide material of the abovementioned formula I or II as the active phase, the standard deviation of the activity, as defined above, of any random samples taken being less than 7° C., in particular less than 3.5° C., particularly preferably less than 2.5° C.

The number of random samples is at least 5, in particular at least 10, for example at least one random sample per 100 kg production quantity. The size of the random sample is preferably about 1 kg, from which, after homogenization, 100 g are taken for the abovementioned activity determination. In the particularly preferred case, the mean value of the activity can be estimated at ±1.6° C. with a reliability of 95% in the case of the production of 1000 kg of product and taking of a random sample from each 100 kg container and subsequent homogenization of the random samples.

For storage or transport, the catalyst batch can suitably be filled into plastic or sheet metal containers which have a capacity of, for example, 50 l or 100 l. In many cases, it is expedient to take a sample of, for example, 1 kg per container for the random sampling discussed above.

Catalysts prepared according to the invention are particularly suitable for the preparation of α,β-monoethylenically unsaturated aldehydes and/or carboxylic acids by gas-phase oxidation of alkanes, alkanols, alkenes and/or alkenals of 3 to 6 carbon atoms. They are furthermore suitable for the preparation of nitriles by ammoxidation, in particular of propene to acrylonitrile and of 2-methylpropene or tert-butanol to methacrylonitrile. They are furthermore suitable for the oxidative dehydrogenation of organic compounds.

The catalysts prepared according to the invention are suitable in particular for the preparation of acrolein, acrylic acid, methacrolein and methacrylic acid, the starting compounds used preferably being propene or 2-methylpropene, tert-butanol or methacrolein. Catalysts prepared according to the invention are particularly suitable for the preparation of acrolein from propene. Oxygen, expediently diluted with inert gases, is used as the oxidizing agent in a manner known per se. Examples of suitable inert gases are nitrogen and steam. Suitable reaction temperatures and reaction pressures are known to a person skilled in the art, it being possible to specify the temperature of from 250 to 450° C. and a pressure of from 0.5 to 4 bar (gauge pressure) as general ranges.

In a further aspect, the present invention relates to a process for the preparation of α,β-monoethylenically unsaturated aldehydes and/or carboxylic acids, in which a gaseous stream of an alkane, alkanol, alkene and/or alkenal of 3 to 6 carbon atoms is passed, at elevated temperatures in the presence of molecular oxygen, through at least one reaction zone which contains a batch of a catalyst having the narrow activity distribution defined above.

The catalysts prepared according to the invention are particularly suitable for the high-load procedure. The loading of the catalyst with the alkane, alkanol, alkene and/or alkenal is at least 160, in particularly at least 165, particularly preferably at least 170, l (S.T.P.) per l of catalyst per hour.

Advantageously, the gaseous stream is passed in succession through a first and a second reaction zone, the temperature of the first reaction zone being from 300 to 330° C. and the temperature of the second reaction zone being from 300 to 365° C. and being at least 5° C. above the temperature of the first reaction zone. The first reaction zone extends as a rule to a conversion of the alkane, alkanol, alkene and/or alkenal of from 40 to 80, preferably from 50 to 70, mol %.

The attached figures and the examples which follow illustrate the invention.

Figure 1:
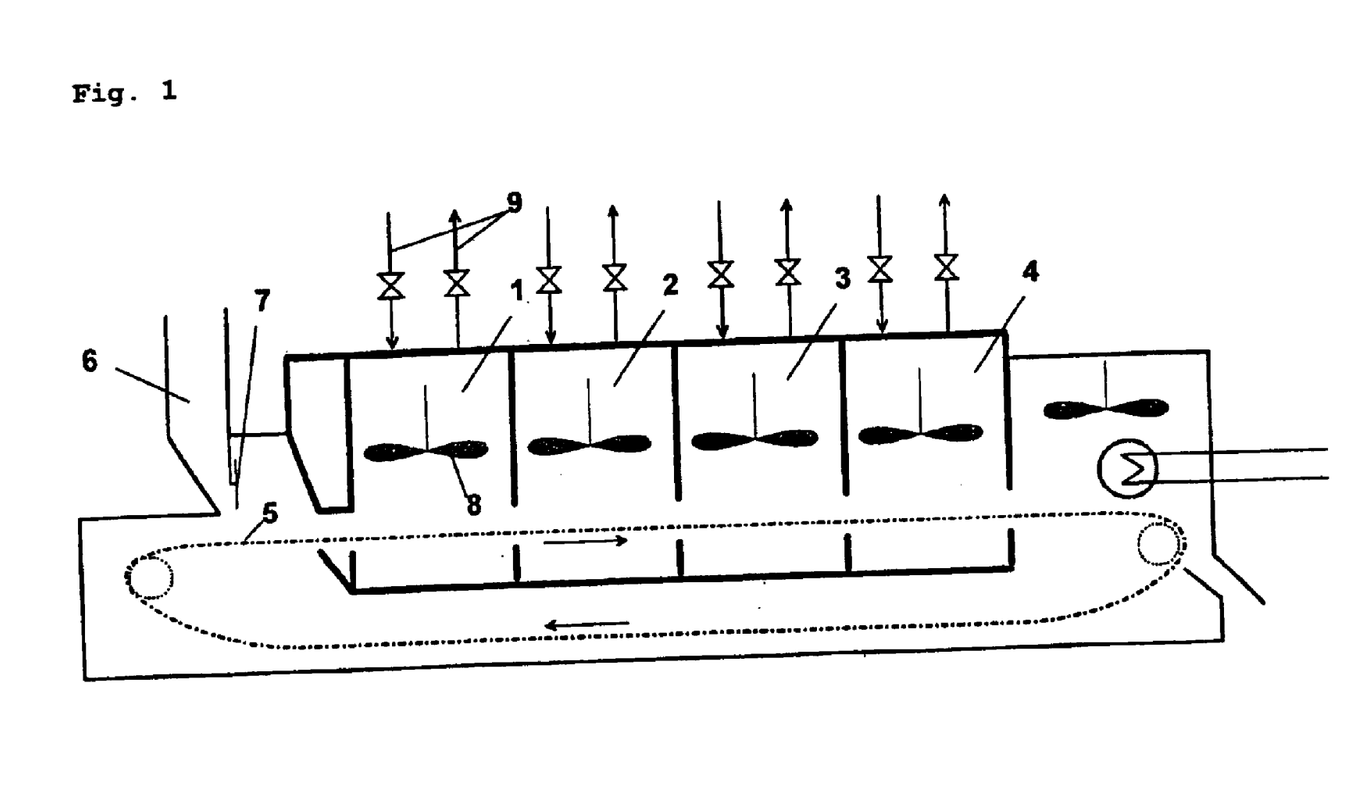
FIG. 1 shows a longitudinal section and FIG. 2 a cross section through a novel belt calcination apparatus.

With reference to FIG. 1, the calcination apparatus shown has four chambers (1, 2, 3, 4), through which a conveyor belt (5) runs. The apparatus has a bunker (6) and a weir (7). Above the conveyor belt (5), fans (8) are present in each chamber. Each chamber is provided with air feed and exhaust means (9). During the operation, the bunker (6) is filled with the particulate catalyst precursor. As a result of the movement of the conveyor belt (5), a layer of the catalyst precursor with constant bed height is withdrawn under the weir (7) and passed in succession through the chambers of the calcination apparatus.

Figure 2:
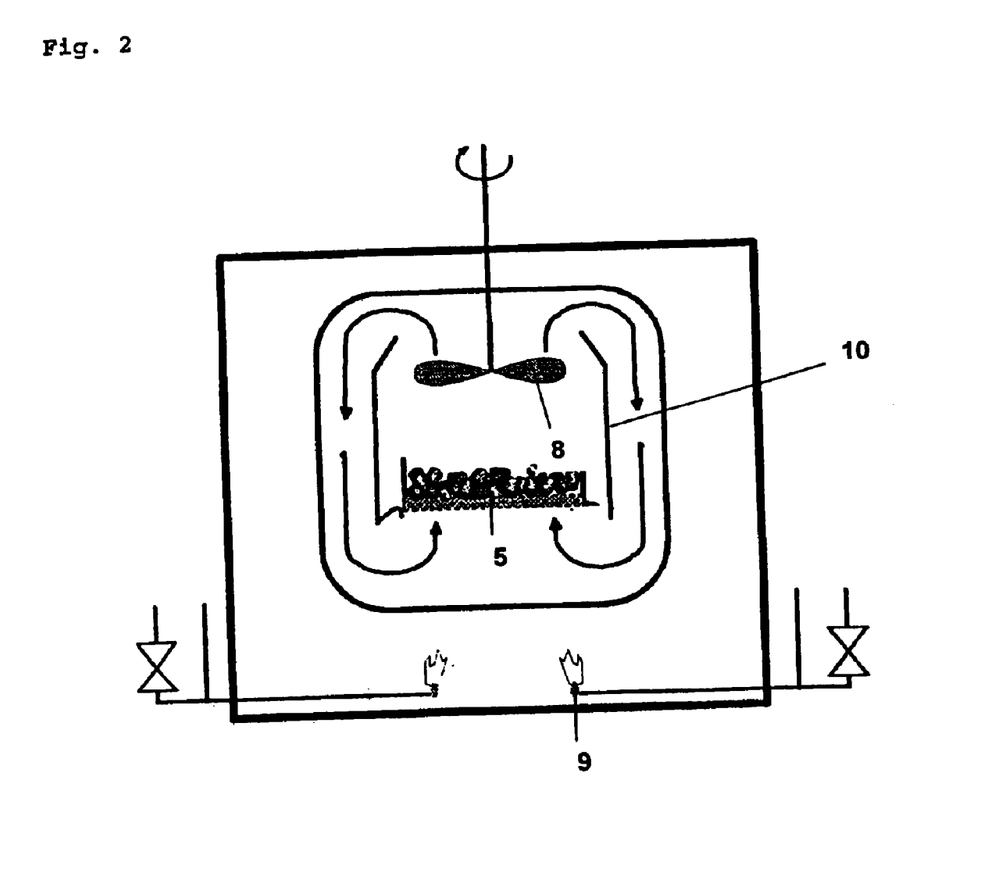

With reference to FIG. 2, each chamber is heated by burners (9). Gas deflection plates (10) which, together with the fans (8), ensure that the circulated atmosphere in each chamber ascends through the gas-permeable conveyor belt (5) and descends again along the walls of the chamber are arranged at the edges of the conveyor belt, substantially in a plane perpendicular to the support area of the conveyor belt.

The catalysts prepared in the examples are characterized by the parameters conversion, acrolein selectivity ($S_{ACR}$) and acrylic acid selectivity ($S_{ACA}$). These parameters were determined as follows:

First, a 15 cm long bed of steatite beads having a diameter of from 2 to 3 mm was introduced into a steel pipe having an internal diameter of 15 mm and an external diameter of 20 mm. 100 g of the catalyst to be tested were then introduced, an average bed height of from 60 to 70 cm resulting. The steel pipe was heated by means of a nitrogen-flushed salt bath over the total length of the bed comprising the catalyst and the steatite beads. At a constant feed gas rate of 100 l (S.T.P.)/h (volume at standard temperature and pressure) and with a composition of 5% by volume of propene, 9.5% by volume of oxygen and 85.5% by volume of nitrogen, the temperature of the salt bath was varied until the propene conversion measured at the exit of the steel pipe was 95%. The propene conversion is defined as follow:

$$conv._{propene}[\%] = \frac{c_{propene,exit}}{c_{propene,entrance}} \times 100$$

In addition, the selectivities with respect to the desired products acrolein and acrylic acid were measured. These are calculated as follows:

$$S_{ACR}[\%] = \frac{c_{ACR,exit}}{c_{propene,entrance} - c_{propene,exit}} \times 100$$

$$S_{ACS}[\%] = \frac{c_{ACS,exit}}{c_{propene,entrance} - c_{propene,exit}} \times 100$$

The selectivity with respect to the desired product is calculated as:

$$S_{DP}[\%] = S_{ACA} + S_{ACR}$$

EXAMPLE 1

First, a starting material of the host phase was prepared. For this purpose, 244 kg of ammonium heptamolybdate were dissolved in portions at 60° C. in 660 l of water, and 1.12 kg of a 47.5% strength by weight potassium hydroxide solution at 20° C. were added while stirring. A second solution was prepared by adding 133.8 kg of an iron nitrate solution (13.8% by weight of iron) to 288.7 kg of a cobalt nitrate solution (12.5% by weight of cobalt), the temperature being kept at 60° C. The second solution was added to the molybdate solution within a period of 30 minutes at 60° C. 15 minutes after the end of the addition, 19.16 kg of silica sol (density 1.36–1.42 g/ml, from pH 8.5 to 9.5, alkali content not more than 0.5% by weight; 46.80% by weight of $SiO_2$) were added to the slurry obtained. Stirring was then carried out for 15 minutes. The slurry obtained was then spray-dried, a powder having a loss on ignition (3 hours at 600° C.) of about 30% by weight being obtained.

A finely divided promoter phase was then prepared. 209.3 kg of tungstic acid (72.94% by weight of tungsten) were then added in portions, while stirring, to 775 kg of a solution of bismuth nitrate in nitric acid (free nitric acid 3–5%, density 1.22–1.27 g/ml, 11.2% by weight of bismuth). The slurry obtained was stirred for 2 hours and was dried by spray-drying. A powder having a loss on ignition (3 hours at 600° C.) of 12% by weight was obtained. This powder was converted into a paste with a small amount of water in a kneader and was converted by means of an extruder into extrudates. These were cut into 6 cm sections and then calcined in a rotary tubular furnace at from 700 to 900° C. for 2 hours, then milled to a mean particle size of about 5 $\mu$m and mixed with 1% by weight of finely divided silica (tapped density 150 g/l, mean particle size 10 $\mu$m, BET surface area 100 m$^2$/g).

The promoter phase prepared beforehand and the starting material of the host phase were mixed, with admixing of 1.5% by weight of graphite (min. 50% by weight<24 $\mu$m; 24 $\mu$m<max. 10% by weight<48 $\mu$m; max. 5% by weight>48 $\mu$m, according to sieve analysis; BET surface area 6–13 m$^2$/g), in a ratio so that a material having stoichiometry $[Bi_2W_2O_9 \times 2WO_3]_{0.5}[Mo_{12}Co_{5.5}Fe_{2.94}Si_{1.59}K_{0.08}O_y]_1$ was obtained. Cylindrical rings having an external diameter of 5 mm, a height of 3 mm and a hole diameter of 2 mm were formed from the material.

The shaped rings were placed in a bed height of from 50 to 70 mm on the belt of a belt calcination apparatus having eight chambers. The chambers each had a fan for producing an air circulation and were thermostated at 180° C., 200° C., 290° C., 390° C., 465° C., 465° C. and 435° C., respectively. Within the chambers, the deviation of the temperature from the setpoint value as a function of time and location was always ≦2° C. The length of the chambers was such that the residence time in the first four chambers was 1.5 h in each case and that in the fifth to eighth chamber was 2 h in each case. In this way, 2.6 t of catalyst were prepared. A 1 kg spot sample was taken from each container having a content of 100 kg and was characterized as described above. The results obtained are shown in Table 1.

TABLE 1

| Consecutive No. | Activity [° C.] | $S_{ACR+ACA}$ [mol %] |
|---|---|---|
| 1 | 315 | 92.7 |
| 2 | 317 | 93 |
| 3 | 317 | 92.3 |
| 4 | 317 | 92.3 |
| 5 | 319 | 92.6 |
| 6 | 319 | 93.6 |
| 7 | 320 | 94 |
| 8 | 322 | 94.7 |
| 9 | 316 | 93.7 |
| 10 | 319 | 94.1 |
| 11 | 321 | 94.1 |
| 12 | 320 | 92.8 |
| 13 | 322 | 93.6 |
| 14 | 321 | 94.9 |
| 15 | 320 | 92.9 |
| 16 | 317 | 93 |
| 17 | 317 | 92.6 |
| 18 | 320 | 93 |
| 19 | 320 | 92.7 |
| 20 | 317 | 92.9 |
| 21 | 318 | 93.9 |
| 22 | 320 | 93.2 |
| 23 | 318 | 92.7 |
| 24 | 322 | 93.9 |
| 25 | 320 | 92.3 |
| 26 | 317 | 94 |
| Mean value | 319 | 93.3 |
| Standard deviation | 0.62% | 0.80% |

COMPARATIVE EXAMPLE 1

The catalyst precursor from Example 1 was calcined in portions of 500 g in a conventional laboratory muffle furnace, in which the temperature fluctuation as a function of time and location was ±3° C., at different required temperatures for the duration of 6 hours. The catalyst properties as a function of the calcination temperature are shown in Table 2.

TABLE 2

| Experiment | $T_{calcination}$ [° C.] | Activity [° C.] | $S_{ACR+ACA}$ [mol %] |
|---|---|---|---|
| 1 | 443 | 314 | 84.5 |
| 2 | 446 | 311 | 92.3 |
| 3 | 449 | 309 | 93.6 |
| 4 | 460 | 321 | 94.7 |
| 5 | 467 | 329 | 96.2 |
| 6 | 471 | 330 | 96.7 |
| 7 | 473 | 330 | 96.6 |
| 8 | 480 | 377 | 96.3 |
| 9 | 480 | 343 | 96.9 |

Table 2 shows that, for example, a temperature difference of 7° C. in the calcination (473° C. and 480° C.) can lead to an activity difference of 47° C. (330° C. and 377° C.). Temperature differences of this order of magnitude are unavoidable in the calcination of large amounts of catalyst by conventional processes, as with the use of tray furnaces. Experiments 8/9 show that different results are obtained even at the same required temperature, since the actual temperature is very inhomogeneous without forced convection, even in the case of 500 g portions.

COMPARATIVE EXAMPLE 2

300 g of the catalyst precursor from Example 1 were distributed over 9 trays arranged one on top of the other on a trolley. The trolley was pushed into a furnace and heated in an air stream. Heating was effected to 185° C. in the course of one hour, the temperature was kept at this value for 1 hour, heating was then effected to 210° C. at a rate of 2° C./min, the temperature was kept at this value for 2 hours, heating was then effected to 250° C. at a rate of 2° C./min, the temperature was kept at this value for 1 hour, heating was then effected to 465° C. at a rate of 5° C./min and the temperature was kept at this value for 6 hours. Said temperatures are the required temperatures set on the furnace. Different temperatures deviating therefrom prevailed on the individual trays of the trolley. From each of these lots, an average sample of all individual trays was taken and was tested as follows.

TABLE 3

| Lots | Activity [° C.] | $S_{ACR+ACA}$ [mol %] |
|---|---|---|
| 1 | 330 | 94.7 |
| 2 | 339 | 95.6 |
| 3 | 324 | 95.2 |
| 4 | 341 | 94.8 |
| 5 | 334 | 94.8 |
| 6 | 344 | 95.1 |
| 7 | 330 | 95 |
| 8 | 340 | 94.9 |
| 9 | 345 | 95.4 |
| 10 | 332 | 94.6 |
| 11 | 332 | 94.2 |
| 12 | 346 | 96.1 |
| 13 | 350 | 96.2 |
| 14 | 332 | 96.3 |
| 15 | 331 | 95.3 |
| 16 | 330 | 94.8 |
| 17 | 330 | 95.1 |
| 18 | 323 | 95.6 |
| 19 | 345 | 95.6 |
| 20 | 335 | 95.6 |
| 21 | 328 | 94.8 |
| 22 | 334 | 95.8 |
| 23 | 329 | 95.5 |
| 24 | 328 | 96.8 |
| 25 | 334 | 95.3 |
| 26 | 342 | 96.5 |
| 27 | 331 | 94.7 |
| 28 | 336 | 94.9 |
| 29 | 326 | 95 |
| 30 | 338 | 95.1 |
| 31 | 326 | 94.2 |
| 32 | 331 | 95.3 |
| 33 | 322 | 94.6 |
| 34 | 330 | 95.6 |
| 35 | 345 | 95.4 |
| 36 | 323 | 96 |
| 37 | 333 | 95.7 |
| 38 | 337 | 95.7 |
| 39 | 340 | 95.8 |
| 40 | 322 | 94 |
| 41 | 343 | 95.1 |
| 42 | 334 | 94.5 |
| 43 | 335 | 95.1 |
| 44 | 336 | 94.4 |
| 45 | 345 | 95.2 |
| 46 | 338 | 95.6 |
| 47 | 343 | 95.3 |
| 48 | 344 | 96.4 |
| 49 | 345 | 95.8 |
| 50 | 348 | 96.3 |
| 51 | 350 | 95.9 |
| 52 | 350 | 96.4 |
| 53 | 346 | 96.1 |
| 54 | 345 | 96.6 |
| 55 | 338 | 95.3 |
| 56 | 344 | 96.1 |
| 57 | 342 | 96.1 |
| 58 | 341 | 96.4 |
| 59 | 348 | 96 |
| 60 | 344 | 94.9 |
| 61 | 348 | 96.2 |
| 62 | 339 | 94.4 |
| 63 | 328 | 93.8 |
| 64 | 340 | 94.9 |
| 65 | 332 | 95.5 |
| 66 | 332 | 95 |
| 67 | 334 | 95.1 |
| 68 | 344 | 95.4 |
| 69 | 334 | 95.1 |
| 70 | 333 | 94.8 |
| 71 | 337 | 94.6 |
| 72 | 337 | 95.5 |
| 73 | 344 | 94.7 |
| 74 | 328 | 94.5 |
| 75 | 325 | 94.3 |
| 76 | 343 | 95.5 |
| 77 | 329 | 95.5 |
| 78 | 340 | 96.3 |
| 79 | 336 | 96 |
| 80 | 342 | 95.3 |
| 81 | 331 | 94.9 |
| 82 | 341 | 95.1 |
| 83 | 335 | 94.7 |
| 84 | 341 | 94.7 |
| 85 | 331 | 94.8 |
| 86 | 329 | 95 |
| 87 | 324 | 94.4 |
| 88 | 333 | 95.6 |
| 89 | 333 | 94.1 |
| 90 | 334 | 94.2 |
| Mean value | 336.3 | 95.3 |
| Standard deviation | 2.168% | 0.703% |

EXAMPLE 2

First, a starting material of the host phase was prepared. For this purpose, 213 kg of ammonium heptamolybdate were dissolved in portions at 60° C. in 600 l of water, and 0.97 kg of a 46.8% strength by weight potassium hydroxide solution at 20° C. were added while stirring. A second solution was prepared by adding 80.2 kg of an iron nitrate solution (14.2% by weight of iron) to 262.9 kg of a cobalt nitrate solution (12.4% by weight of cobalt), the temperature being kept at 60° C. The second solution was added to the molybdate solution within a period of 30 minutes at 60° C. 15 minutes after the end of the addition, 19.16 kg of silica sol (density 1.36–1.42 g/ml, from pH 8.5 to 9.5, alkali content not more than 0.5% by weight; 46.80% by weight of $SiO_2$) were added to the slurry obtained. Stirring was then carried out for 15 minutes. The slurry obtained was then spray-dried, a powder having a loss on ignition (3 hours at 600° C.) of about 30% by weight being obtained.

The preparation of the finely divided promoter phase was carried out as in Example 1.

The promoter phase prepared beforehand and the starting material of the host phase were mixed, with admixture of 1.5% by weight of graphite, in a ratio so that a material having a stoichiometry $[Bi_2W_2O_9 \times 2WO_3]_{0.5}$ $[Mo_{12}Co_{5.5}Fe_{2.0}Si_{1.59}K_{0.08}O_y]_1$ was obtained. The cylindrical rings having an external diameter of 5 mm, a height of 2 mm and a hole diameter of 2 mm were formed from the material. The shaped rings were calcined as described in Example 1. The characterization of the catalyst obtained was also carried out as described in Example 1. The results obtained are shown in Table 4.

TABLE 4

| Consecutive No. | Activity [° C.] | $S_{ACR+ACA}$ [mol %] |
|---|---|---|
| 1 | 320 | 93.7 |
| 2 | 316 | 92.6 |
| 3 | 322 | 93.1 |
| 4 | 322 | 92.9 |
| 5 | 321 | 92.3 |
| 6 | 319 | 94.0 |
| 7 | 320 | 92.5 |
| 8 | 317 | 92.1 |
| 9 | 320 | 92.5 |
| 10 | 318 | 92.8 |
| 11 | 320 | 92.7 |
| 12 | 318 | 92.2 |
| 13 | 321 | 93.9 |
| 14 | 318 | 93.5 |
| 15 | 322 | 93.9 |
| 16 | 324 | 93.8 |
| 17 | 317 | 92.5 |
| 18 | 318 | 92.9 |
| 19 | 322 | 93.9 |
| 20 | 321 | 92.7 |
| Mean value | 320 | 93.0 |
| Standard deviation | 0.67% | 0.69% |

COMPARATIVE EXAMPLE 3

The catalyst precursor from Example 2 was calcined in portions of 500 g in a conventional laboratory muffle furnace, in which the temperature fluctuation as a function of time and location was ±3° C., at different required temperatures for the duration of 6 hours. The catalyst properties as a function of the calcination temperature are shown in Table 5.

TABLE 5

| Experiment | $T_{calcination}$ [° C.] | Activity [° C.] | $S_{ACR+ACA}$ [mol %] |
|---|---|---|---|
| 1 | 440 | 316 | 83 |
| 2 | 445 | 312 | 92.1 |
| 3 | 450 | 310 | 93.4 |
| 4 | 460 | 321 | 94.2 |
| 5 | 467 | 327 | 96.4 |
| 6 | 471 | 330 | 96.7 |
| 7 | 475 | 333 | 96.8 |
| 8 | 477 | 340 | 97.5 |
| 9 | 480 | 370 | 96.5 |

EXAMPLE 3

213 kg of ammonium heptamolybdate were dissolved in portions at 60° C. in 600 l of water, and 0.97 kg of a 46.8% strength by weight potassium hydroxide solution at 20° C. was added while stirring. A second solution was prepared by adding 116.25 kg of an iron nitrate solution (14.2% by weight of iron) to 333.7 kg of a cobalt nitrate solution (12.4% by weight of cobalt), the temperature being kept at 30° C. and stirring being carried out for a further 30 minutes up to the end of the addition. At 60° C., 112.3 kg of a bismuth nitrate solution (11.2% of bismuth) are metered into the iron/cobalt solution. The second solution was added to the molybdate solution within a period of 30 minutes at 60° C. 15 minutes after the end of the addition, 19.16 kg of silica sol (46.80% by weight of $SiO_2$) were added to the slurry obtained. Stirring was then carried out for 15 minutes. The slurry obtained was then spray-dried, a powder having a loss on ignition (3 hours at 600° C.) of about 30% by weight being obtained.

The composition of the active material is $Mo_{12}Co_7Fe_{2.94}Bi_{0.6}Si_{1.59}K^{0.08}O_z$.

After the spray-drying, the starting material was mixed with 1.5% by weight of graphite, compacted and formed into cylindrical rings having an external diameter of 5 mm, a height of 3 mm and a hole diameter of 2 mm. The shaped rings were calcined in a belt calcination apparatus having eight chambers. The chambers were thermostated at 160° C., 200° C., 230° C., 270° C., 380° C., 430° C., 500° C. and 500° C., respectively. The residence time was 2 hours each in the first to fourth chambers and 5 hours in the fifth to eighth chambers. The characterization of the catalyst obtained was carried out as in Example 1. The results obtained are shown in Table 6.

TABLE 6

| Consecutive No. | Activity [° C.] | $S_{ACR+ACA}$ [mol %] |
|---|---|---|
| 1 | 319 | 95.6 |
| 2 | 318 | 95.7 |
| 3 | 317 | 95.7 |
| 4 | 317 | 95.3 |
| 5 | 319 | 95.5 |
| 6 | 320 | 95.4 |
| 7 | 319 | 95.7 |
| 8 | 319 | 95.4 |
| 9 | 319 | 95.4 |
| 10 | 318 | 95.4 |
| 11 | 319 | 95.4 |
| 12 | 321 | 95.8 |
| 13 | 320 | 95.8 |
| 14 | 320 | 95.7 |
| 15 | 323 | 96.0 |
| 16 | 318 | 95.8 |
| 17 | 321 | 96.1 |
| Mean value | 319 | 95.6 |
| Standard deviation | 0.48% | 0.24% |

COMPARATIVE EXAMPLE 4

The catalyst precursor from Example 3 was calcined in portions of 500 g in a conventional laboratory muffle furnace, in which the temperature fluctuation as a function of time and location was about ±3° C., at different required temperatures for the duration of 6 hours. The catalyst properties as a function of the calcination temperature are shown in Table 7.

TABLE 7

| Experiment | $T_{calcination}$ [° C.] | Activity [° C.] | $S_{ACR+ACA}$ [mol %] |
|---|---|---|---|
| 1 | 461 | 309 | 94.3 |
| 2 | 462 | 307 | 95.2 |
| 3 | 466 | 313 | 94.3 |
| 4 | 467 | 317 | 95.1 |
| 5 | 469 | 313 | 95.4 |
| 6 | 471 | 316 | 96 |
| 7 | 479 | 324 | 96.7 |
| 8 | 485 | 326 | 96.5 |
| 9 | 491 | 324 | 96.9 |

TABLE 7-continued

| Experiment | $T_{calcination}$ [° C.] | Activity [° C.] | $S_{ACR+ACA}$ [mol %] |
|---|---|---|---|
| 10 | 493 | 331 | 97.3 |
| 11 | 500 | 347 | 97.4 |

EXAMPLE 4

Example 1 was repeated, but a belt calcination apparatus having 12 zones was used. The temperature and residence time in the first eight zones were as stated in Example 1. Zones 9 to 12 were all thermostated at 500° C., and the residence time was 2 hours in each case. The atmosphere in chambers 9 to 12 substantially comprised nitrogen. In this way, 3.5 t of catalyst were prepared. A 1 kg spot sample was taken from each container having a content of 100 kg and was characterized as described above. The results obtained are shown in Table 8.

TABLE 8

| Consecutive No. | Activity [° C.] | $S_{ACR+ACA}$ [mol %] |
|---|---|---|
| 1 | 315 | 94.7 |
| 2 | 316 | 93 |
| 3 | 317 | 94.3 |
| 4 | 317 | 94.3 |
| 5 | 319 | 94.6 |
| 6 | 318 | 93.8 |
| 7 | 319 | 94.6 |
| 8 | 317 | 93.7 |
| 9 | 314 | 93.4 |
| 10 | 318 | 95 |
| 11 | 320 | 95.1 |
| 12 | 320 | 95.2 |
| 13 | 318 | 94.8 |
| 14 | 317 | 94.3 |
| 15 | 314 | 94 |
| 16 | 318 | 94.8 |
| 17 | 318 | 94.8 |
| 18 | 318 | 94.7 |
| 19 | 317 | 94.3 |
| 20 | 314 | 94 |
| 21 | 319 | 94.5 |
| 22 | 320 | 95 |
| 23 | 320 | 94.8 |
| 24 | 318 | 94.7 |
| 25 | 317 | 94.6 |
| 26 | 316 | 94.7 |
| 27 | 319 | 95 |
| 28 | 317 | 94.5 |
| 29 | 319 | 95 |
| 30 | 314 | 94.4 |
| 31 | 316 | 94.6 |
| 32 | 317 | 94.7 |
| 33 | 317 | 94.8 |
| 34 | 318 | 94.7 |
| 35 | 319 | 95 |
| Mean value | 317.4 | 94.5 |
| Standard deviation | 0.552% | 0.515% |

EXAMPLE 5

191.5 kg of $MoO_3$, 45.6 kg of CoO, 27.2 kg of $Fe_2O_3$, 10.4 kg of $SiO_2$, and 0.4 kg of $K_2O$ were thoroughly mixed in succession in a mixer; the promoter phase prepared in Example 1 was then added in a ratio so that a material having a stoichiometry $[(Bi_2W_2O_9 \times 2WO_3)_{0.5}/Mo_{12}Co_{5.5}Fe_{3.0}Si_{1.6}K_{0.08}O_y]$ was obtained, said material being formed to cylindrical rings having an external diameter of 5 mm, a height of 2 mm and a hole diameter of 2 mm. The shaped rings were calcined in a belt calcination apparatus which had three chambers which were thermostated at 270° C., 465° C. and 465° C., respectively. The residence time per chamber was 3 hours. In this way, 2.5 t of catalyst were prepared. A 1 kg spot sample was taken from each container having a content of 100 kg and was characterized as described above. The results obtained are shown in Table 9.

TABLE 9

| Consecutive No. | Activity [° C.] | $S_{ACR+ACA}$ [mol %] |
|---|---|---|
| 1 | 317 | 93.7 |
| 2 | 318 | 94 |
| 3 | 317 | 94.3 |
| 4 | 319 | 95 |
| 5 | 317 | 94 |
| 6 | 320 | 94.5 |
| 7 | 320 | 94 |
| 8 | 321 | 94.8 |
| 9 | 317 | 93 |
| 10 | 316 | 93 |
| 11 | 317 | 93.4 |
| 12 | 319 | 93.8 |
| 13 | 315 | 93 |
| 14 | 317 | 93.6 |
| 15 | 318 | 93.8 |
| 16 | 319 | 93.8 |
| 17 | 319 | 94 |
| 18 | 318 | 93.5 |
| 19 | 317 | 93.4 |
| 20 | 315 | 93.8 |
| 21 | 319 | 93 |
| 22 | 316 | 93.6 |
| 23 | 320 | 93.8 |
| 24 | 318 | 93 |
| 25 | 317 | 92.8 |
| Mean value | 317.8 | 93.7 |
| Standard deviation | 0.495% | 0.609% |

EXAMPLE 6

Example 3 was repeated, but the amounts of the components were chosen so that the chemical composition $Mo_{12}CO_7Fe_3Bi_{1.0}Si_{1.6}K_{0.08}O_z$ was obtained. The calcination was carried out in a belt calcination apparatus having eight zones which were thermostated at 160° C., 210° C., 240° C., 290° C., 380° C., 515° C., 515° C. and 400° C., respectively. A 1 kg spot sample was taken from each container having a content of 100 kg and was characterized as described above. The results obtained are shown in Table 10.

TABLE 10

| Consecutive No. | Activity [° C.] | $S_{ACR+ACA}$ [mol %] |
|---|---|---|
| 1 | 317 | 94.9 |
| 2 | 318 | 95.8 |
| 3 | 319 | 94.7 |
| 4 | 317 | 95.1 |
| 5 | 319 | 95.2 |
| 6 | 320 | 94.8 |
| 7 | 321 | 96 |
| 8 | 318 | 94.8 |
| 9 | 319 | 94.8 |
| 10 | 317 | 95.7 |
| 11 | 316 | 95 |
| 12 | 318 | 95.6 |
| 13 | 318 | 95 |
| 14 | 319 | 95.7 |
| 15 | 317 | 94.9 |
| 16 | 319 | 95.3 |
| 17 | 318 | 95 |
| 18 | 317 | 94.7 |

TABLE 10-continued

| Consecutive No. | Activity [° C.] | $S_{ACR+ACA}$ [mol %] |
|---|---|---|
| 19 | 318 | 95 |
| 20 | 319 | 95.6 |
| 21 | 319 | 95.7 |
| 22 | 320 | 95.7 |
| 23 | 320 | 95.8 |
| 24 | 318 | 95 |
| 25 | 317 | 94.8 |
| Mean value | 318.3 | 95.2 |
| Standard deviation | 0.382% | 0.440% |

EXAMPLE 7

114.4 kg of $MoO_3$, 34.5 kg of CoO, 15.8 kg of $Fe_2O_3$, 6.3 kg of $SiO_2$, 9.2 kg of $Bi_2O_3$ and 0.2 kg of $K_2O$ were homogeneously mixed in succession in a mixer. The mixture was formed to cylindrical rings having an external diameter of 5 mm, a height of 3 mm and a hole diameter of 2 mm.

The shaped rings were calcined in a belt calcination apparatus having three chambers which were thermostated at 350° C., 510° C. and 510° C., respectively. The residence time per chamber was 2.5 hours. In this way, 2.5 t of catalyst were prepared. A 1 kg spot sample was taken from each container having a content of 100 kg and was characterized as described above. The results obtained are shown Table 11.

TABLE 11

| Consecutive No. | Activity [° C.] | $S_{ACR+ACA}$ [mol%] |
|---|---|---|
| 1 | 316 | 94.9 |
| 2 | 318 | 95.8 |
| 3 | 317 | 94.7 |
| 4 | 319 | 95.1 |
| 5 | 316 | 95.2 |
| 6 | 320 | 94.8 |
| 7 | 318 | 96 |
| 8 | 321 | 94.8 |
| 9 | 318 | 94.8 |
| 10 | 315 | 95.7 |
| 11 | 317 | 95 |
| 12 | 319 | 95.6 |
| 13 | 315 | 95 |
| 14 | 318 | 95.7 |
| 15 | 318 | 94.9 |
| 16 | 319 | 95.3 |
| 17 | 319 | 95 |
| 18 | 320 | 94.7 |
| 19 | 317 | 95 |
| 20 | 315 | 95.6 |
| 21 | 319 | 95.7 |
| 22 | 315 | 95.7 |
| 23 | 320 | 95.8 |
| 24 | 318 | 95 |
| 25 | 316 | 94.8 |
| Mean value | 317.7 | 95.2 |
| Standard deviation | 0.557% | 0.440% |

We claim:

1. A process for the preparation of a catalyst, comprising:
preparing a particulate catalyst precursor which contains oxides and/or compounds of elements other than oxygen which constitute a multimetal oxide material, wherein said compounds of elements other than oxygen can be converted into oxides, and
converting said particulate catalyst precursor by calcination into a catalytically active form by passing a stream of said particulate catalyst precursor at substantially constant speed through at least one calcination zone for calcination and passing a gas stream through the stream of said particulate catalyst precursor perpendicularly to the direction of advance of the stream of said particulate catalyst precursor in the calcination zone,
wherein a maximum variation of the temperature as a function of time is ≦5° C.;
wherein a maximum local temperature difference in the calcination zone is ≦5° C.; and
wherein said catalyst comprises an active phase of said multimetal oxide material.

2. The process as claimed in claim 1, wherein the multimetal oxide material contains
at least one first metal selected from the group consisting of molybdenum, tungsten and mixtures thereof, and
at least one second metal selected from the group consisting of bismuth, tellurium, antimony, tin, copper, iron, cobalt, nickel and mixtures thereof.

3. The process as claimed in claim 2, wherein the multimetal oxide material has the formula I or II, (I)

(II)

wherein
$X^1$ is bismuth, tellurium, antimony, tin and/or copper,
$X^2$ is molybdenum and/or tungsten,
$X^3$ is an alkali metal, thallium and/or samarium,
$X^4$ is an alkaline earth metal, nickel, cobalt, copper, manganese, zinc, tin, cadmium and/or mercury,
$X^5$ is iron, chromium, cerium and/or vanadium,
$X^6$ is phosphorus, arsenic, boron and/or antimony,
$X^7$ is a rare earth metal, titanium, zirconium, niobium, tantalum, rhenium, ruthenium, rhodium, silver, gold, aluminum, gallium, indium, silicon, germanium, lead, thorium and/or uranium,
a is from 0.01 to 8,
b is from 0.1 to 30,
c is from 0 to 4,
d is from 0 to 20,
e is from 0 to 20,
f is from 0 to 6,
g is from 0 to 15,
h is from 8 to 16,
x and y are numbers which are determined by the valency and frequency of the elements other than oxygen in I,
p and q are numbers whose ratio p/q is from 0.1 to 10,
$X^8$ is cobalt and/or nickel,
$X^9$ is silicon and/or aluminum,
$X^{10}$ is an alkali metal,
is from 0.1 to 2,
k is from 2 to 10,
l is from 0.5 to 10,
m is from 0 to 10,
n is from 0 to 0.5,
z is a number which is determined by the valency and frequency of the elements other than oxygen in II.

4. The process as claimed in claim 3, wherein said multimetal oxide material has the formula I.

5. The process as claimed in claim 3, wherein said multimetal oxide material has the formula II.

6. The process as claimed in claim 1, comprising passing the particulate catalyst precursor through at least two calcination zones which are thermostated at different temperatures.

7. The process as claimed in claim 1, wherein the maximum variation of the temperature in the calcination zone as a function of time is ≦3° C.

8. The process as claimed in claim 7, wherein the maximum variation of the temperature in the calcination zone as a function of time is $\leq 2°$ C.

9. The process as claimed in claim 1, wherein the maximum local temperature difference in the calcination zone is $\leq 3°$ C.

10. The process as claimed in claim 9, wherein the maximum local temperature difference in the calcination zone is $\leq 2°$ C.

11. The process as claimed in claim 1, which is performed in a belt calcinations apparatus comprising at least one heatable chamber, a gas-permeable conveyor belt passing through the chamber, and, located in said chamber, a fan for producing a gas circulation on the basis of forced convection.

* * * * *